United States Patent [19]

Nunokawa

[11] Patent Number: 4,544,248

[45] Date of Patent: Oct. 1, 1985

[54] OPHATHALMOSCOPIC CAMERA HAVING A FOCUS DETECTING SYSTEM

[75] Inventor: Kazuo Nunokawa, Tokyo, Japan

[73] Assignee: Tokyo Kogaku Kikai Kabushiki Kaisha, Tokyo, Japan

[21] Appl. No.: 582,062

[22] Filed: Feb. 21, 1984

[30] Foreign Application Priority Data

Feb. 18, 1983 [JP] Japan .................................. 58-25949

[51] Int. Cl.[4] .......................... G03B 29/00; A61B 3/14
[52] U.S. Cl. ........................................ 354/62; 351/206
[58] Field of Search ................... 354/62; 351/206–208

[56] References Cited

U.S. PATENT DOCUMENTS 3,925,793 12/1975 Matsumara et al. ............. 351/206 X
4,265,518  5/1981 Matsumara ........................... 351/206
4,422,735 12/1983 Shimizu et al. ........................ 354/62

*Primary Examiner*—William B. Perkey

*Attorney, Agent, or Firm*—Brumbaugh, Graves, Donohue & Raymond

[57] ABSTRACT

An ophthalmoscopic camera comprising a photographing optical system including an objective lens adapted to be positioned opposite to a patient's eye with a working distance and an image plane on which an image of fundus of the patient's eye is formed, an illuminating optical system for projecting a beam of illuminating light to the patient's eye, a focus detecting optical system including a mark projecting system having a mark plate formed with at least one mark and located conjugate with the image plane of the photographing optical system with respect to the objective lens and an optical system for optically projecting the mark through the pupil of the patient's eye to the eye fundus. The mark projecting system includes a beam rotating device for rotating the mark projecting beam about the mark projecting optical axis.

9 Claims, 8 Drawing Figures

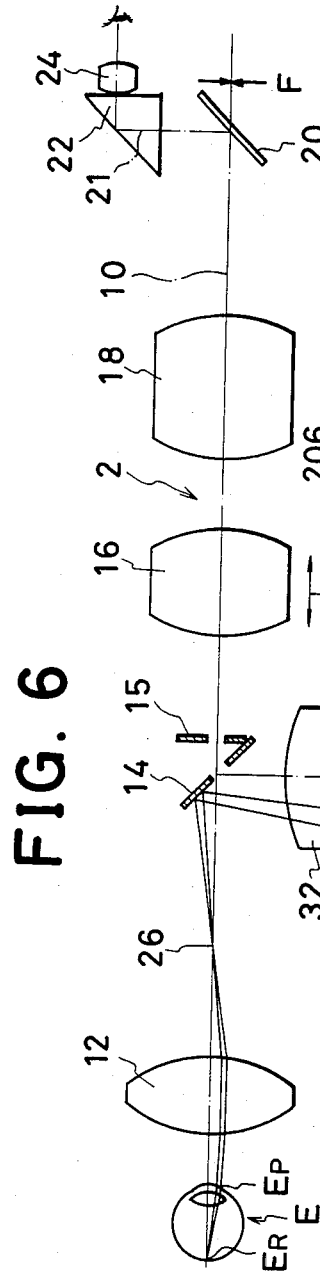
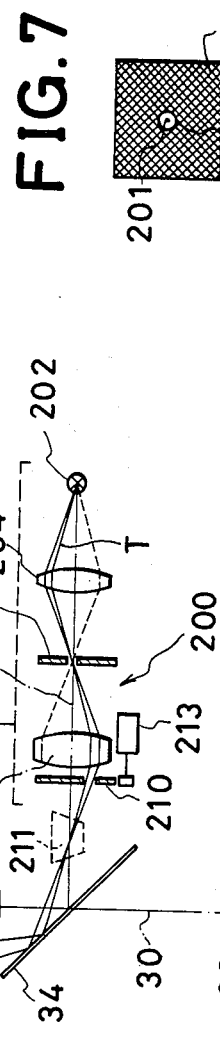
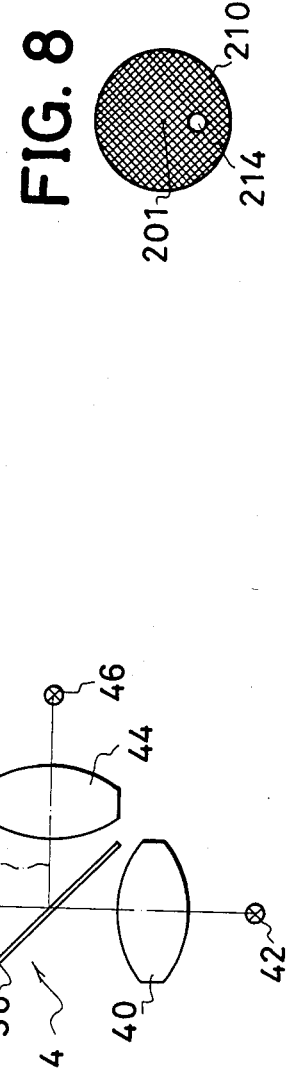

4,544,248

OPHATHALMOSCOPIC CAMERA HAVING A FOCUS DETECTING SYSTEM

BACKGROUND OF INVENTION

1. Field of Invention

The present invention relates to an ophthalmoscopic camera, and more particularly to an ophthalmoscopic camera having focus detecting means. More specifically, the present invention pertains to an ophthalmoscopic camera having focus detecting means including mark projecting means for projecting a mark to a patient's eye for detecting focus conditions of the camera.

2. Description of Prior Art

Hithertofore, there has been proposed for the purpose of facilitating focus adjustments to provide an ophthalmoscopic camera with a focus detecting system. An example of such focus detecting system includes a mark projecting optical system having a mark plate located in conjugate with the image plane of the photographing optical system with respect to the objective lens of the camera and a split-prism device for dividing a beam of light from the mark plate into a pair of beams emitting in different angles. The pair of beams are passed respectively through a pair of apertures located in conjugate with the pupil of the patient's eye so that the beams form images of the apertures at the pupil of the patient's eye and an image of the mark at the eye fundus. Thus, an operator can know the focusing condition of the camera on the eye fundus by the image of the mark. In order to make it easy to judge the focus condition by the mark image, it is desirable to make the distance between the aperture images at the pupil as large as possible within the confine of the pupil.

It should however be noted that the ophthalmoscopic camera is used not only with its optical axis in alignment with the optical axis of the patient's eye but also with its optical axis inclined with respect to the optical axis of the patient's eye so as to take pictures of peripheral portions of the patient's eye. Where the optical axis of the camera is inclined with respect to the optical axis of the patient's eye, the pupil of the patient's eye has an elliptical configuration as seen in the direction of the optical axis of the camera. Thus, when the two beams of light projected through the pair of apertures are arranged in a direction of minor axis of the ellipse, the beams may be blocked by the patient's eye.

DESCRIPTION OF THE INVENTION

Object of the Invention

It is therefore an object of the present invention to provide an ophthalmoscopic camera having a focus detecting system in which a pair of mark projecting beams can be projected with a large convergent angle even when the camera is oriented obliquely with respect to the patient's eye.

Another object of the present invention is to provide a focus detecting system for an ophthalmoscopic camera in which the mark projecting beams can be arranged in a direction of major axis of the ellipse defined by the pupil of the patient's eye when the camera is oriented obliquely with respect to the patient's eye.

SUMMARY OF THE INVENTION

In order to accomplish the above and other objects, the present invention provides an ophthalmoscopic camera comprising a photographing optical system including objective lens means adapted to be positioned opposite to a patient's eye with a working distance and an image plane on which an image of fundus of the patient's eye is focused, an illuminating optical system for projecting a beam of illuminating light to the patient's eye, a focus detecting optical system including mark projecting means having a mark plate formed with at least one mark and located conjugate with said image plane of the photographing optical system with respect to said objective lens means and means for optically projecting said mark through pupil of the patient's eye to the fundus of the eye, said mark projecting means including means for varying area of beam of light for projecting the mark at the pupil of the patient's eye. In one aspect of the present invention, the mark plate includes a mark in the form of an elongated aperture. The mark projecting beam from the elongated aperture may be splitted into two beams emitting in different angles and projected through the pupil of the patient's eye on the retina to form an image of the aperture under a focused condition. Alternatively, the mark plate may include a circular aperture through which a mark projecting beam is emitted with an angle with respect to the optical axis of the mark projecting means. Means is then provided for rotating the mark projecting beam about the optical axis of the mark projecting means so that beam is moved continuously along a circular path at the pupil of the patient's eye.

BRIEF DESCRIPTION OF DRAWINGS

FIG. 6 is a diagrammatical illustration of an optical system in accordance with a further embodiment of the present invention; and FIGS. 7 and 8 illustrates examples of mark plates.

DESCRIPTION OF PREFERRED EMBODIMENTS

Figure 1:
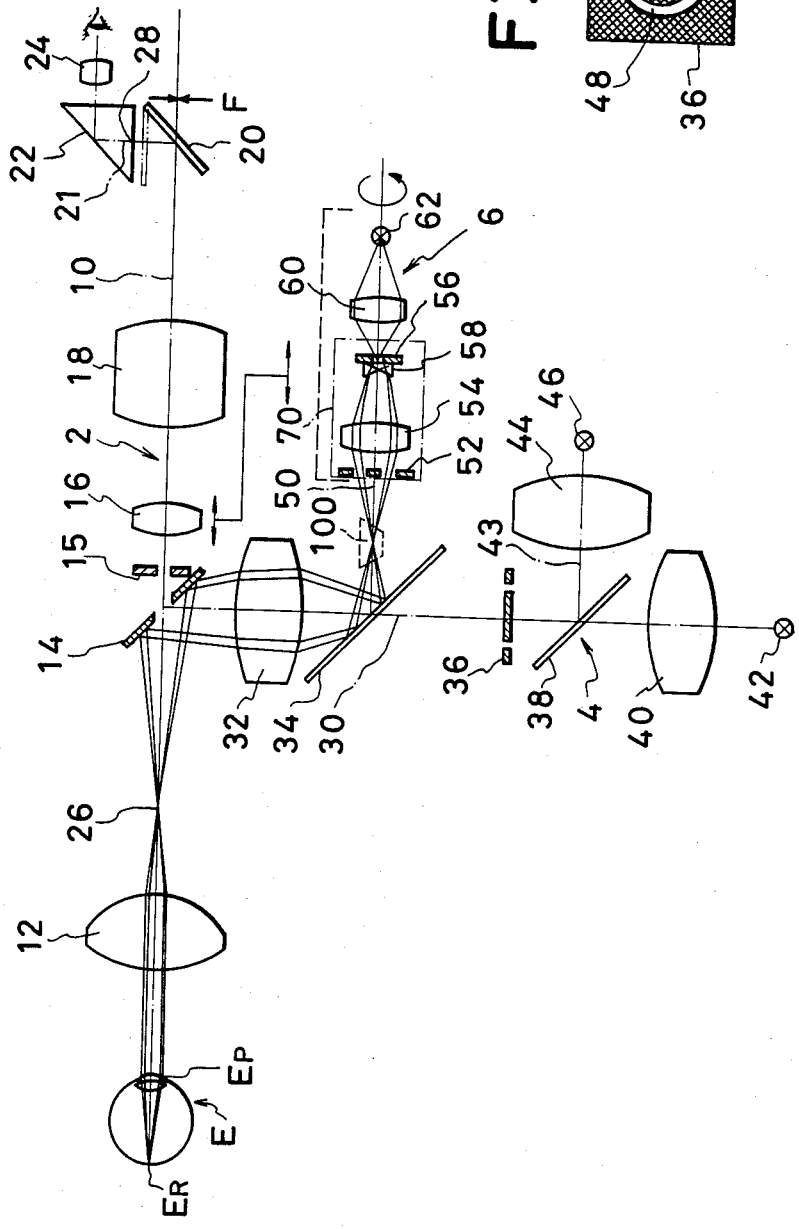
FIG. 1 is a diagrammatical illustration of an optical system of an ophthalmoscopic camera in accordance with one embodiment of the present invention.

Referring now to the drawings, particularly to FIG. 1, the optical system of the ophthalmoscopic camera shown therein includes a photographing optical system 2, an illuminating optical system 4 and a focus detecting system 6.

The photographing optical system 2 includes an objective lens 12 having an optical axis 10 and adapted to be located opposite a patient's eye E with a proper distance which is referred to as a working distance. Behind the objective lens 12, there is an aperture plate 15 which is located in conjugate with the pupil Ep of the patient's eye E with respect to the objective lens 12. The photographing optical system 2 further includes a focusing lens 16 and a relay lens 18 which are arranged in this order along the optical axis 10. An image plane or photographing film plane F is provided so that an image of the fundus or retina $E_R$ of the patient's eye E is once formed by the objective lens 12 at an image point 26 and then formed by the focus lens 16 and the relay lens 18 on the film plane F. In order to focus the image on the film plane F, the focusing lens 16 is movable along the optical axis 10 as shown by an arrow in FIG. 1. A retratable mirror 20 is provided in front of the film plane F for reflecting beams of light from the relay lens upwards along a reflecting optical axis 21. Above the mirror 20, there is provided a prism 22 having an image plane 28 which is conjugate with the film plane F. An eyepiece 24 is provided to observe the image formed on the image plane 28.

Figure 2:
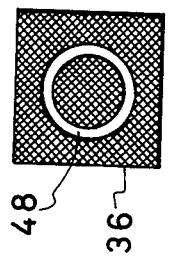
FIG. 2 is a front view of a ring-shaped aperture used in the illuminating optical system.

The illuminating optical system 4 includes an observing light source 46 such as a tungsten lamp 46 and a condenser lens 44 for directing the light from the lamp 46 along an illuminating optical axis 43. There is further provided a photographing light source 42 such as a xenon lamp and a condenser lens 40 for directing the light from the light source 42 along an illuminating optical axis 30 which intersects the optical axis 10 in the photographing optical system 2. A half mirror 38 is provided on the optical axis 30 to reflect the light along the optical axis to the direction along the optical axis. A ring-shaped aperture plate 36 is provided on the optical axis 30 and has a ring-shaped aperture 48 as shown in FIG. 2. There are further provided a relay lens 32 and an apertured mirror 14 in the illuminating optical system 4. The apertured mirror 14 is located obliquely on the optical axis 10 of the photographing optical system 2 and substantially conjugate with the cornea of the patient's eye with respect to the objective lens 12. The aperture plate 36 is conjugate with the pupil Ep of the patient's eye E so that the light which has passed through the ring-shaped aperture 48 is reflected by the apertured mirror 14 and then passed through the pupil Ep to illuminate the retina $E_R$. For observation, the light source 46 is used and for photographing the light source 42 is energized.

Figure 3:
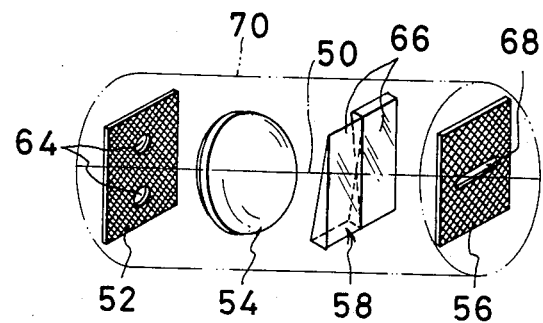
FIG. 3 is a perspective view showing one example of the mark projecting system in the embodiment shown in FIG. 1.

The focusing optical system 6 includes a half mirror 34 obliquely located on the illuminating optical axis 30 between the relay lens 32 and the ring-shaped aperture plate 36. There are provided a light source 62 and a condenser lens 60 for directing the light from the source 62 toward the half mirror 34 along a mark projecting optical axis 50. Along the optical axis 50, there is a mark plate 56 which has a mark in the form of an elongated slit 68 as shown in FIG. 3. The mark plate 56 is associated with a split image prism 58 which comprises a pair of wedge-shaped prisms 66 having oppositely sloped surfaces. Between the split image prism 58 and the half mirror 34, there are provided a relay lens 54 and an aperture plate 52 having a pair of apertures 64 located symmetrically with each other with respect to the mark projecting optical axis 50. The aperture plate 52 is located in conjugate with the pupil Ep of the patient's eye E. The aperture plate 52, the relay lens 54, the split image prism 58, the mark plate 56, the condenser lens 60 and the light source 62 are assembled together so that they can be moved as a unit along the optical axis 50 and also together with the focusing lens 16 of the photographing optical system 2 with the mark plate 56 always maintained in conjugate with the film plane F.

Figure 4:
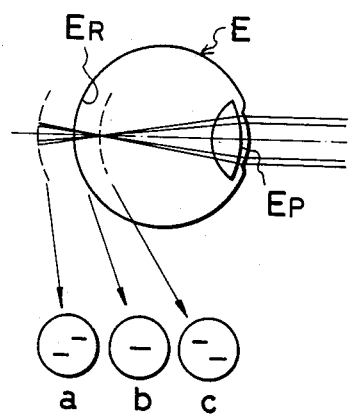
FIG. 4 is a diagrammatical illustration of the relationship between the mark image and the focus condition.
Figure 5:
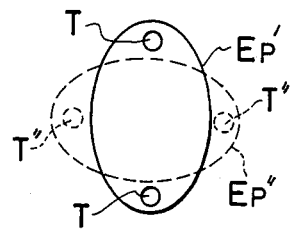
FIG. 5 is a diagrammatical illustration of mark projecting light beams on the pupil of the patient's eye.

The beam of light from the light source 62 is passed through the elongated aperture 68 in the mark plate 56 and divided by the prism 58 into two beams emitting in different angles. The beams of light are then passed through the relay lens 54 and respectively through the apertures 64 in the plate 52 to be projected through the objective lens 12 to the patient's eye E. As shown in FIG. 4, the mark projecting beams pass through the pupil Ep in the vicinity of the periphery thereof and form an image of the aperture 68 on the retina $E_R$. In case where the aperture plate 56 is conjugate with the retina $E_R$, or in other words, if the film plane F is conjugate with the retina $E_R$, the image of the aperture 68 will be in the form of a single line as shown by b in FIG. 4. However, in case where such conjugate relationship is not established, the image of the mark aperture 68 will be split as shown by a or c in FIG. 4.

Where the camera is placed with the optical axis 10 of the objective lens 12 aligned with the optical axis of the patient's eye E, the pupil Ep will be substantially circular as seen in the direction of projection of the mark aperture 68. However, where the camera is obliquely located to take photographs of peripheral portions of the retina $E_R$, the pupil Ep will assume an elliptical configuration as shown by Ep' or Ep'' in FIG. 5. If the mark projecting beams are arranged along the major axis of the ellipse as shown by T in FIG. 5 but if they are along the minor axis of the ellipse as shown by T'', the beams may not be able to pass through the pupil Ep. The spacing between the beams may be decreased to avoid the problem, however, such solution will adversely affect on the ability of detecting focus condition.

In the embodiment shown in FIG. 1, the aperture plate 52, the relay lens 54, the split image prism 58 and the mark plate 56 are mounted in a single housing 70 which is rotatable about the optical axis 50 so that the mark projecting beams can be rotated about the optical axis 50. Thus, it is always possible to arrange the mark projecting beams along the major axis of the ellipse defined by the pupil Ep. Alternatively, the mark projecting system may include an image rotating prism 100 located on the projecting optical axis 50 so that the mark projecting beams may be rotated about the optical axis 50 as desired.

Referring now to FIG. 6 which shows a further embodiment of the present invention, it will be noted that the ophthalmoscopic camera shown therein has a photographing optical system 2 and an illuminating optical system 4 which are substantially the same as those in the previous embodiment so that detailed descriptions will be omitted by designating corresponding parts with the same reference numerals. The camera of this embodiment includes a focusing optical system 200 having a mark projecting optical axis 201 and comprised of a light source 202 and a condenser lens 204 for directing the light from the source 202 toward the half mirror 34 located obliquely on the illuminating optical axis 30. Along the mark projecting optical axis 201, there is provided a mark plate 206 having an aperture 212 which is coaxial with the optical axis 201 as shown in FIG. 7. Further, a relay lens 208 and an aperture plate 210 are arranged on the optical axis 201. The aperture plate 210 has an aperture 214 which is offset from the optical axis 201 as shown in FIG. 8. The mark plate 206 is conjugate with the film plane F whereas the aperture plate 210 is conjugate with the pupil Ep of the patient's eye E. The aperture plate 210 is rotatable about the optical axis 201 and a motor 213 is provided for continuously rotating the aperture plate 210. The light source 202, the condenser lens 204, the mark plate 206, the relay lens 208 and the aperture plate 210 are assembled together so that they can be moved as a unit along the optical axis 201 and also with the focusing lens 16 of the photographing optical system 2 so that the mark plate 206 is maintained always in conjugate with the film plane F. In operation, the aperture plate 210 is continuously rotated by the motor 213 while the mark projecting light beam is being projected. Under a focused condition, a single spot image is formed on the eye fundus $E_R$ but a circularly moving image is formed when the system is out of focus.

When the camera is oriented obliquely with respect to the patient's eye E, the mark projecting beam may be partially blocked by the eye in areas adjacent to the minor axis of the ellipse defined by the pupil Ep. However, the beam can pass through the pupil Ep in areas adjacent to the major axis of the ellipse so that it is possible to produce a mark image which is sufficient to judge the focus condition. In this embodiment, the aperture plate 210 may not necessarily be rotated but an image rotating prism 211 may be provided between the plate 210 and the half mirror 34 and the prism may be rotated continuously.

The invention has thus been shown and described with reference to specific embodiments, however, it should be noted that the invention is in no way limited to the details of the illustrated arrangements but changes and modifications may be made without departing from the scope of the appended claims.

I claim:

1. An ophthalmoscopic camera comprising a photographing optical system including objective lens means adapted to be positioned opposite to a patient's eye with a working distance and an image plane on which an image of fundus of the patient's eye is formed, an illuminating optical system for projecting a beam of illuminating light to the patient's eye, a focus detecting optical system including mark projecting means having a mark plate formed with at least one mark and located conjugate with said image plane of the photographing optical system with respect to said objective lens means and means for optically projecting said mark through pupil of the patient's eye to the fundus of the eye, said mark projecting means including means for varying a position of at least one mark-projecting beam of light with respect to the axis of the objective lens where the beam passes the objective lens, and with respect to the pupil of the patient's eye.

2. An opthalmoscopic camera in accordance with claim 1 in which said mark projecting means includes means for producing at least two mark projecting beams emitting in different angles.

3. An ophthalmoscopic camera in accordance with claim 2 in which said beam producing means includes a split image prism.

4. An ophthalmoscopic camera in accordance with claim 2 which further includes means for rotating said mark projecting means about an optical axis of said focus detecting optical system.

5. An ophthalmoscopic camera in accordance with claim 4 in which said rotating means is means for rotatably mounting said beam producing means.

6. An ophthalmoscopic camera in accordance with claim 4 in which said rotating means is an image rotating optical element.

7. An ophthalmoscopic camera in accordance with claim 1 in which said mark projecting means has a projecting optical axis and includes means for producing a mark projecting beam emitting with an angle with respect to the projecting optical axis, means being provided for continuously rotating said mark projecting beam about said projecting optical axis.

8. An ophthalmoscopic camera in accordance with claim 7 in which said beam producing means includes an aperture offset from said projecting optical axis and adapted to be located conjugate with the pupil of the patient's eye under a focused condition, said beam rotating means includes means for rotating said aperture about the projecting optical axis.

9. An ophthalmoscopic camera in accordance with claim 7 in which said beam rotating means is an image rotating optical element.

* * * * *